(12) United States Patent
Ignon et al.

(10) Patent No.: US 6,942,649 B2
(45) Date of Patent: Sep. 13, 2005

(54) MICRODERMABRASION FLUID APPPLICATION SYSTEM AND METHOD

(75) Inventors: Roger G. Ignon, Redondo Beach, CA (US); Alejandro Herrera, Corona, CA (US); William Cohen, Long Beach, CA (US)

(73) Assignee: Edge Systems Corporation, Signal Hill, CA (US)

( * ) Notice: Subject to any disclaimer, the term of this patent is extended or adjusted under 35 U.S.C. 154(b) by 224 days.

(21) Appl. No.: 10/315,478

(22) Filed: Dec. 10, 2002

(65) Prior Publication Data

US 2003/0167032 A1 Sep. 4, 2003

Related U.S. Application Data

(60) Provisional application No. 60/361,045, filed on Mar. 1, 2002.

(51) Int. Cl.[7] .......................... A61M 35/00; A61B 17/50
(52) U.S. Cl. ..................... 604/289; 290/606; 290/131
(58) Field of Search ................................ 604/289, 290; 606/131–133

(56) References Cited

U.S. PATENT DOCUMENTS

| | | |
|---|---|---|
| 4,572,187 A | 2/1986 | Schetrumpf |
| 5,037,432 A | 8/1991 | Molinari |
| 5,100,412 A | 3/1992 | Rosso |
| 5,154,696 A | 10/1992 | Shearing |
| 5,207,234 A | 5/1993 | Rosso |
| 5,354,307 A | 10/1994 | Porowski |
| 5,810,842 A | 9/1998 | Di Fiore |
| 5,954,730 A | 9/1999 | Bernabei |
| 5,971,999 A | 10/1999 | Naldoni |
| 6,019,749 A | 2/2000 | Fields |
| 6,039,745 A | 3/2000 | Di Fiore |
| 6,080,165 A | 6/2000 | DeJacma |
| 6,162,232 A | 12/2000 | Shadduck |
| 6,196,982 B1 | 3/2001 | Ball |
| 6,235,039 B1 | 5/2001 | Parkin |
| 6,241,739 B1 | 6/2001 | Waldron |
| 6,250,996 B1 | 6/2001 | Metcalf |
| 6,299,620 B1 | 10/2001 | Shadduck |
| 6,319,211 B1 | 11/2001 | Ito |
| 6,391,034 B1 | 5/2002 | Adamson |
| 6,423,078 B1 | 7/2002 | Bays |
| 6,432,113 B1 | 8/2002 | Parkin |
| 6,629,983 B1 * | 10/2003 | Ignon .......................... 606/131 |
| 6,652,888 B2 * | 11/2003 | Rhoades ...................... 424/691 |
| 2001/0023351 A1 | 9/2001 | Eilers |

* cited by examiner

Primary Examiner—John J. Calvert
Assistant Examiner—Linh Truong
(74) Attorney, Agent, or Firm—Myers Dawes Andras and Sherman LLP

(57) ABSTRACT

A growth factor delivery system for use in connection with microdermabrasion includes a source of growth factors. The growth material may be dry and thus mixed in with the abrasion media. The dry growth material would therefore be applied to the target skin area simultaneously with the abrasion media by a single handpiece. The growth material may comprise a fluid to be delivered by a separate handpiece. The fluid source may be within the handpiece or external thereto. The fluid source may be contained in a removable cartridge adapted to fit within the handpiece. Thus, a method and system is provided for using disposable cartridges of growth fluids.

25 Claims, 5 Drawing Sheets

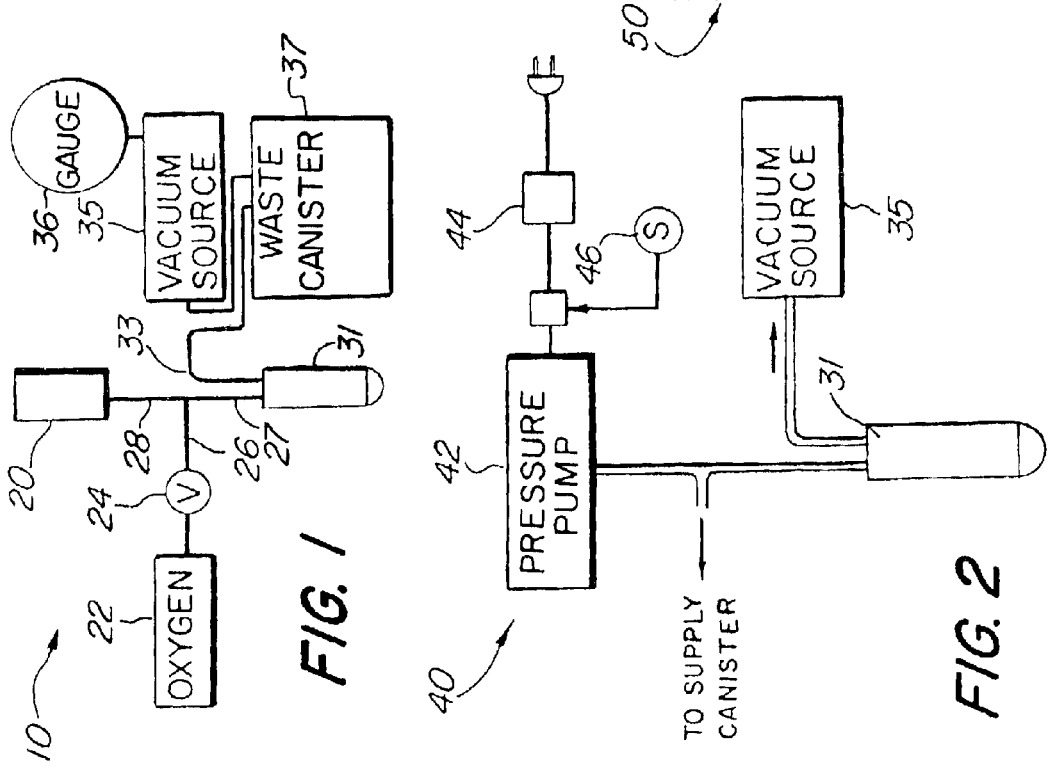

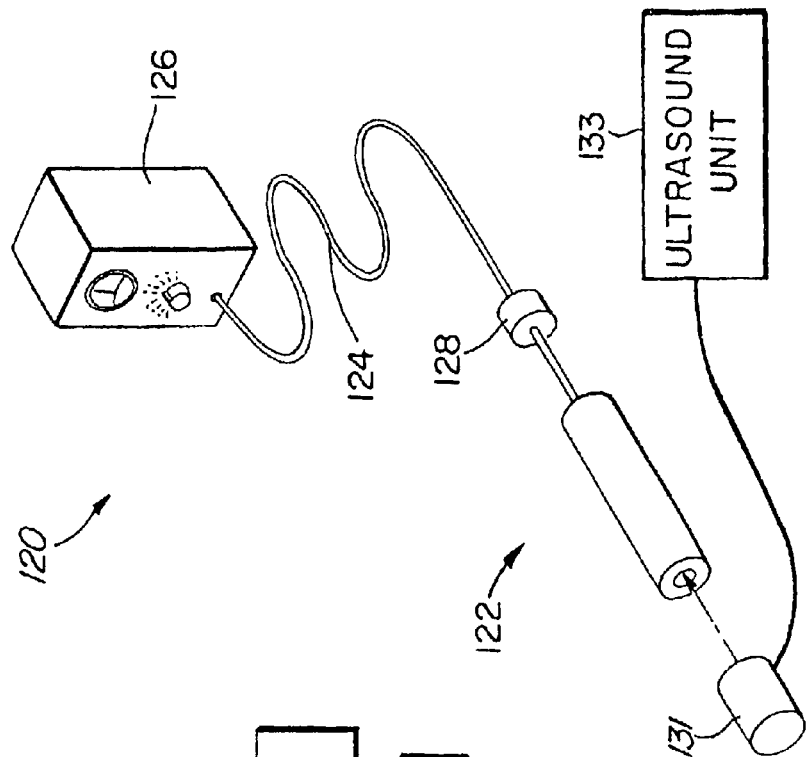
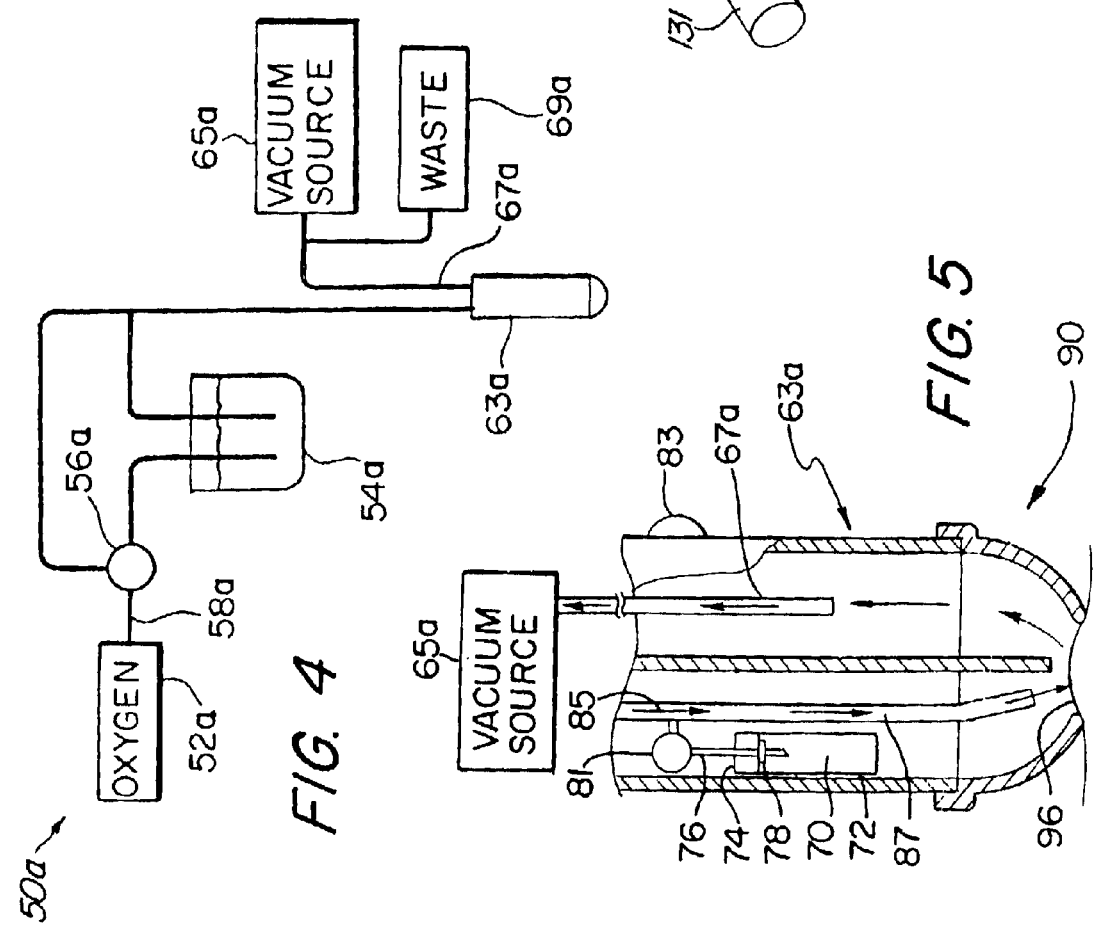

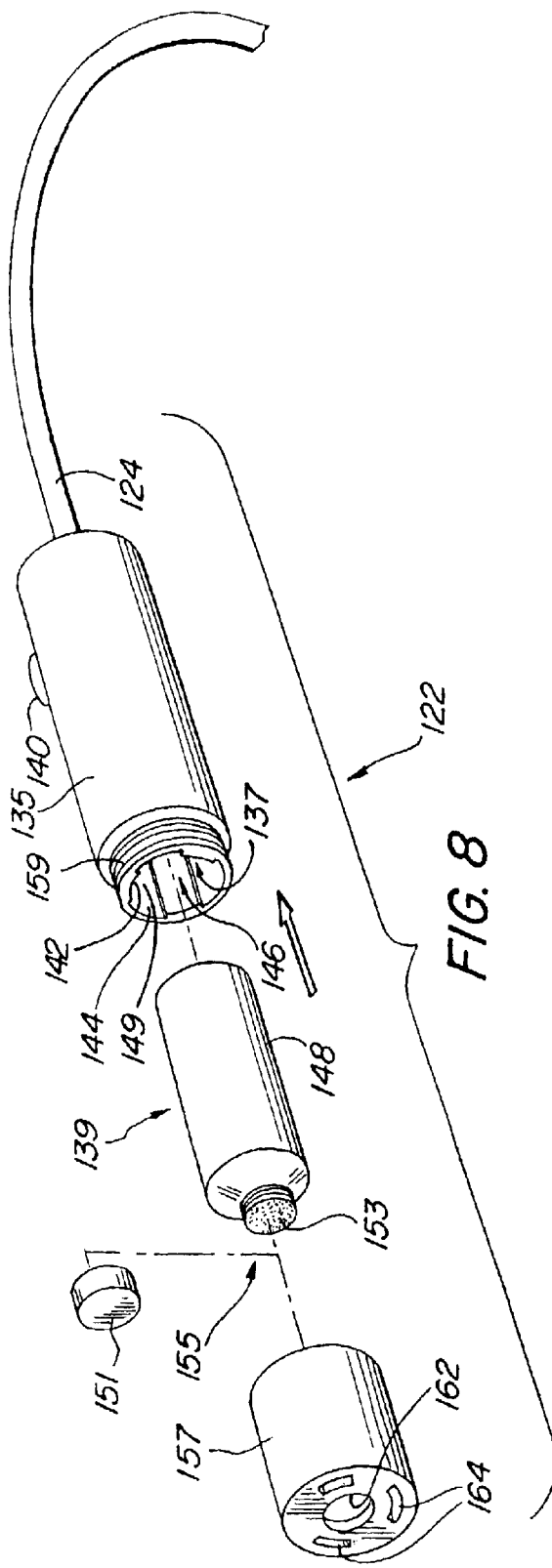
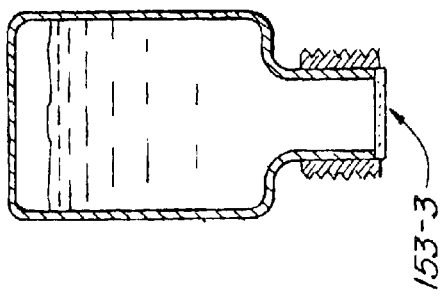
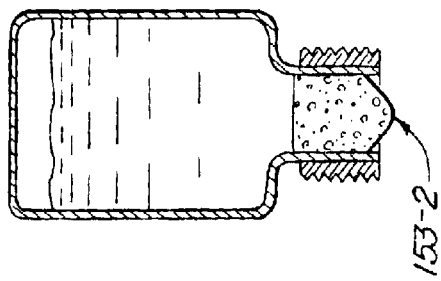
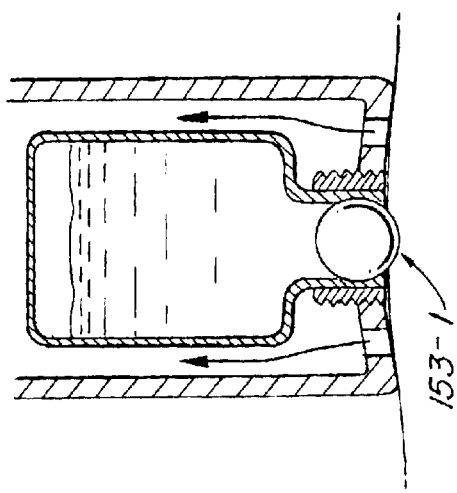

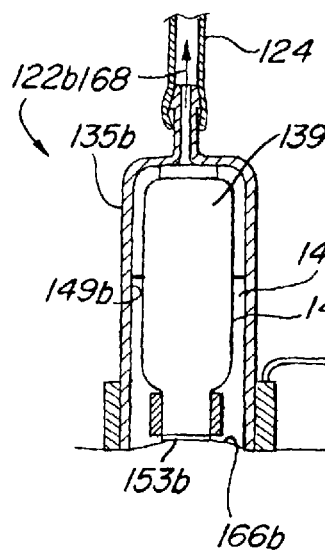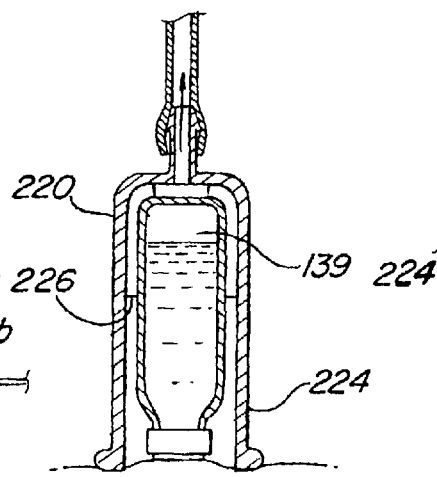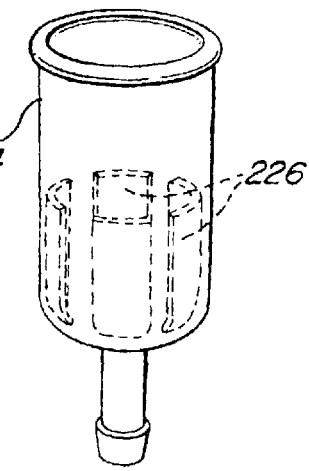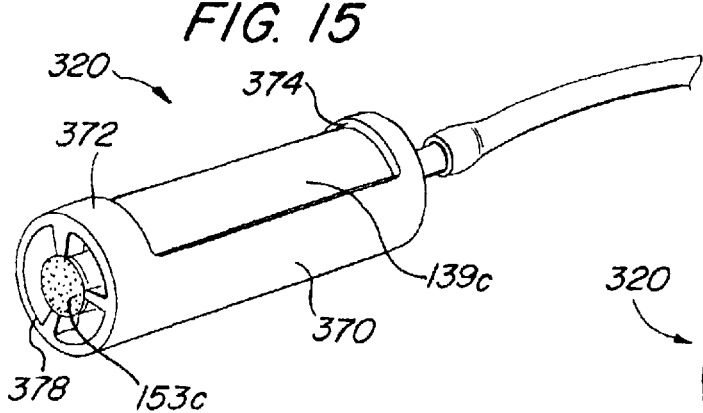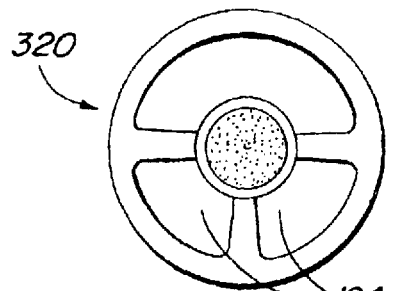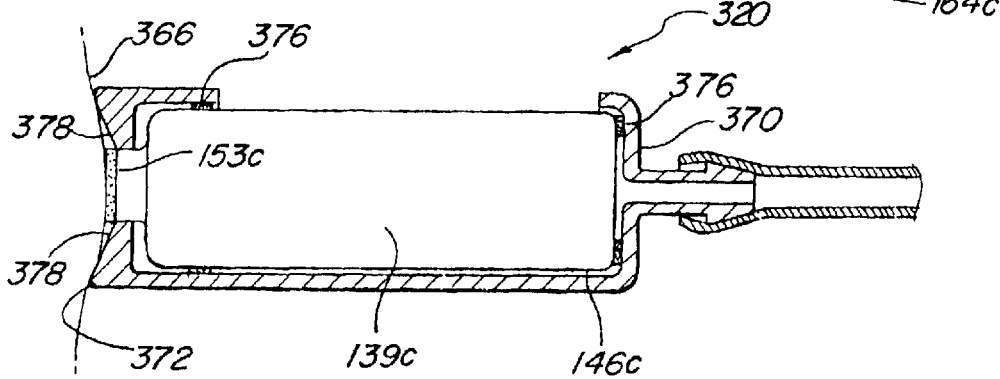

MICRODERMABRASION FLUID APPPLICATION SYSTEM AND METHOD

RELATED APPLICATION

This application relates to and claims priority from U.S. Provisional Application Ser. No. 60/361,045 filed on Mar. 1, 2002, entitled "HUMAN GROWTH FACTOR DELIVERY SYSTEM," the disclosure of which is incorporated herein by reference.

BACKGROUND OF THE INVENTION

1. Field of the Invention

The invention relates generally to skin or surface abrasion apparatus and methods.

2. Description of Prior Art and Related Information

It is often desirable to abrade the outer layer or epidermis of the skin in order to smooth or blend scars, or blemishes caused by acne for example. In a technique known as microdermabrasion, a sand or grit is carried by an air flow which is directed against the skin. The momentum of the grit tends to wear away two to three cell layers of the skin with each pass of a handpiece. Since microdermabrasion is intended to wear away cell layers of the skin, the process tends to create a wound on the target skin area.

Consequently, a need exists for quickly healing the wounded area caused by the abrasion procedure in order to reduce trauma as well as to yield the desired result—skin that is not only aesthetically pleasing, but healthy as well.

SUMMARY OF THE INVENTION

In accordance with the present invention, structures and associated methods are disclosed which address these needs.

In one aspect, a microdermabrasion apparatus comprises a supply of abrasion media, a supply of growth material, at least one handpiece to apply the abrasion media and the growth material to a target area, and a mechanism for removing the abrasion media from the target area. The growth material may be dry and thus mixed in with the abrasion media. The growth material, or additive, comprises growth factors such as vitamins. A source of oxygen is in communication with the handpiece. A valve is provided to control a flow of the oxygen to the handpiece. The mechanism for removal may comprise a vacuum source disposed downstream from the handpiece. The apparatus may further comprise a positive pressure source disposed upstream from the handpiece.

In another aspect, a microdermabrasion system is provided comprising separate handpieces for the microdermabrasion media and the growth material. The system comprises a first supply of microdermabrasion media and a first handpiece in communication with the first supply of microdermabrasion media. A second handpiece is provided in communication with a second supply of growth material. A mechanism alternatively causes a first flow of the microdermabrasion media through the first handpiece and a second flow of the growth material through the second handpiece. A control unit is coupled to the first handpiece and the second handpiece. The control unit includes a switch to alternate operation of the mechanism between the first handpiece and the second handpiece.

The second supply of growth material may comprise a liquid having at least one growth factor. A source of oxygen may be coupled to the liquid. A valve is coupled to the source of oxygen and adapted to control a flow of oxygen to the liquid. The mechanism may comprise a vacuum source coupled to both the first handpiece and the second handpiece, which vacuum source may be housed in the control unit. The first supply of microdermabrasion media is also disposed in the control unit. The second supply of growth material may be disposed in the control unit or carried by the second handpiece.

A fluid delivery apparatus is also provided for applying a fluid to a target skin area. A cartridge is disposed substantially within a handpiece. The cartridge holds a supply of fluid and includes an applicator adapted to apply the fluid to a target skin area. The supply fluid contains at least one growth factor. A vacuum source is coupled to the handpiece and adapted to draw the fluid out of the cartridge and through the applicator. The applicator may comprise a sponge, a roller, a membrane, or any other material suitable for applying fluid onto skin.

The handpiece comprises a housing adapted to slidingly receive the cartridge and a beveled distal portion adapted to contact the target skin area. The distal portion may include vacuum ports. The distal portion is adapted to form a seal with the target skin area. The housing may include a removable cap to facilitate assembly and removal of the container. A space, or fluid passageway, is defined within the housing exterior to the container. The space is in communication with the vacuum source. The space is sealed off from any area exterior to the handpiece when the housing forms the seal with the target skin area.

A method is provided for microdermabrading skin. The method comprises the steps of abrading a target skin area with microdermabrasion media, applying growth material to the target skin area, retrieving the microdermabrasion media from the target skin area, and retrieving at least a portion of the growth material from the target skin area. Where the growth material is dry, the method further comprises the step of mixing the dry growth material with the microdermabrasion media prior to the applying step.

The step of abrading a target skin area with microdermabrasion media comprises the step of applying the microdermabrasion media to the target skin area with a first handpiece. The step of applying growth material to the target skin area comprises the step of applying the growth material to the target skin area with a second handpiece. The method further comprises the step of disposing the growth material in an aqueous solution, and disposing the aqueous solution with the growth material upstream from the second handpiece. The method further comprises the step of carrying the aqueous solution with the second handpiece.

The step of disposing the aqueous solution with the growth material within the second handpiece comprises the step of retaining the aqueous solution with a cartridge carried by the handpiece. The method further comprises the step of disposing an applicator on a distal end of the cartridge. The step of applying the growth material to the target skin area with the second handpiece comprises contacting the target skin with the applicator. A sponge applicator, roller applicator, membrane applicator, or other suitable applicators may be employed.

In summary, a growth factor delivery system for use in connection with microdermabrasion includes a source of growth factors. The growth material may be dry and thus mixed in with the abrasion media. The dry growth material would therefore be applied to the target skin area simultaneously with the abrasion media by a single handpiece. The growth material may comprise a fluid or a gel to be delivered by a separate handpiece. The fluid source may be within the handpiece or external thereto. The fluid source may be contained in a removable cartridge adapted to fit within the handpiece. Thus, a method and system is provided for using disposable cartridges of growth fluids.

The invention, now having been briefly summarized, may be better visualized by turning to the following drawings wherein like elements are referenced by like numerals.

BRIEF DESCRIPTION OF THE DRAWINGS

FIG. 1 is a schematic view of a preferred embodiment of a microdermabrasion apparatus;

FIG. 2 is a schematic view of a further preferred embodiment of microdermabrasion system having a positive pressure pump;

FIG. 3 is a schematic view of a preferred embodiment of a "wet" growth factor delivery apparatus;

FIG. 4 is a schematic view of a further preferred embodiment of a wet growth factor delivery apparatus;

FIG. 5 is an enlarged schematic view of a handpiece of the preferred wet growth factor delivery apparatus illustrated in FIG. 4;

FIG. 6 is a schematic view of a combined system including a microdermabrasion apparatus and a wet growth factor delivery apparatus;

FIG. 7 is a schematic view of a further preferred embodiment of a wet growth factor delivery apparatus;

FIG. 8 is an exploded, perspective view of a handpiece of the preferred system illustrated in FIG. 7;

FIG. 9 is a partially removed side elevation view of a cartridge having a first preferred applicator;

FIG. 10 is a partially removed side elevation view of a cartridge having a second preferred applicator;

FIG. 11 is a partially removed side elevation view of a cartridge having a third preferred applicator;

FIG. 12 is a cross-sectional view of the preferred delivery apparatus of FIG. 7 in operation;

FIG. 13 is an axial cross-sectional view of a further preferred handpiece for a fluid delivery system;

FIG. 14 is a perspective view of a housing of the handpiece of FIG. 13;

FIG. 15 is a perspective view of a further preferred handpiece for a fluid delivery system;

FIG. 16 is an axial cross-sectional view of the handpiece of FIG. 15;

FIG. 17 is an end view of the handpiece of FIG. 15; and

Figure 18:
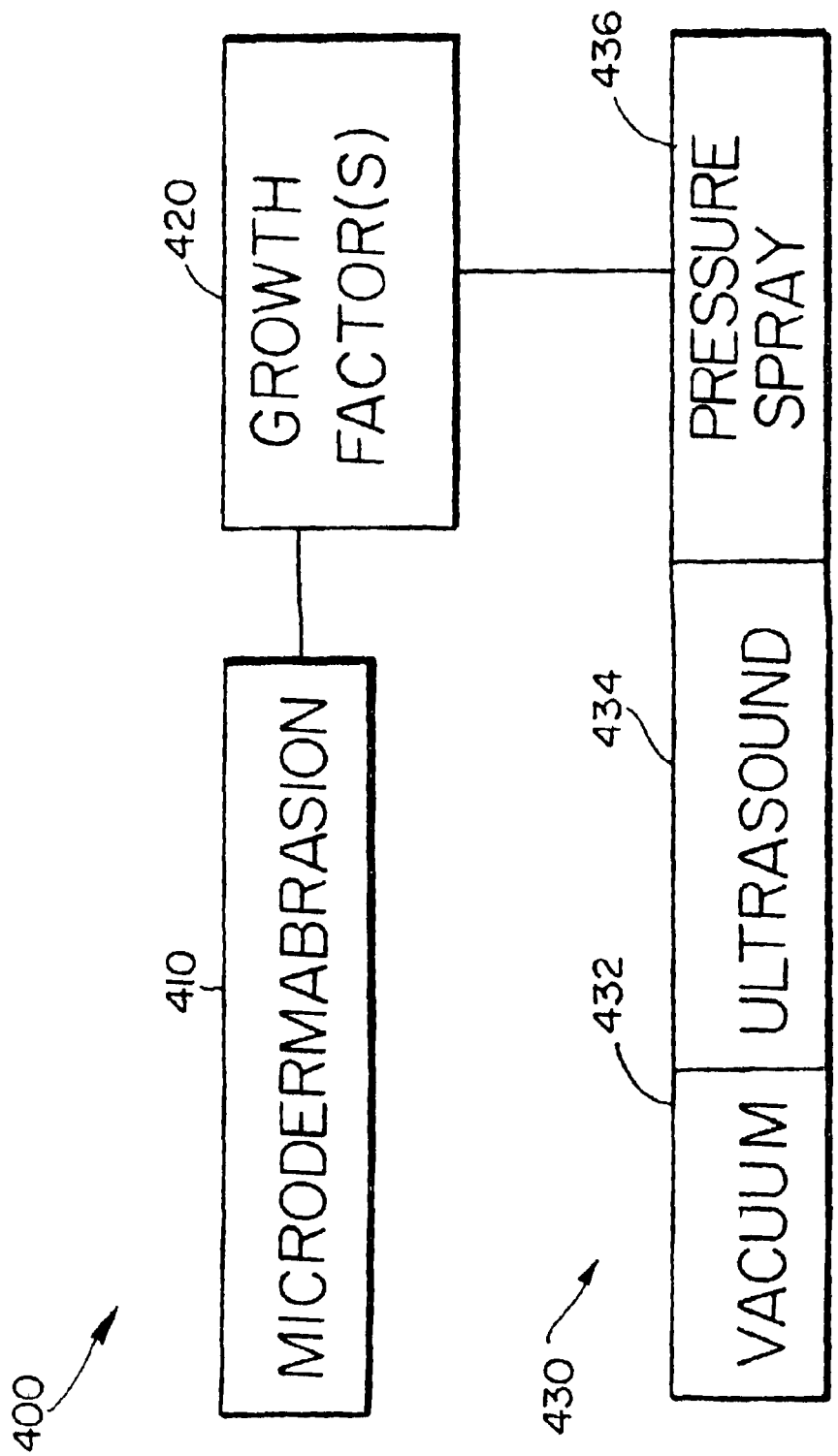
FIG. 18 is a block diagram illustrating various modules that may be combined with microdermabrasion to form a combined system.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

FIG. 1 is a schematic view of a microdermabrasion apparatus 10 according to the invention. The apparatus 10 includes a unique supply 20 of microdermabrasion media that is preferably composed of cutting materials, such as aluminum oxide, crystals or other microdermabrasive materials, and one or more growth factors or vitamins. Unlike conventional microdermabrasion approaches which include a supply that consists of merely cutting material, it will be appreciated that the inclusion of growth factors facilitates healing of the treated area. With growth factors mixed in with the cutting materials, the growth factors are applied to the cut skin area simultaneously with the abrasive materials. By way of example and not by way of limitation, the vitamins may include any combination of vitamins A, C, or E. Further by way of example and not by way of limitation, the growth factor may include a product that can be purchased under the trade name of Nouricel manufactured by Advanced Tissues Sciences.

An oxygen supply 22 provides oxygen which mixes with the incoming flow of media and air from the media supply 20. A control valve 24 is coupled to an oxygen inlet conduit 26 leading from the oxygen supply 22 to a primary inlet conduit 27. A media inlet conduit 28 extends from the media supply 20 to the primary inlet conduit 27 which is coupled to a handpiece 31. A return conduit 33 is coupled to the handpiece 31 and a vacuum pump 35. A valve 34 may be coupled to the return conduit 33. The vacuum pump 35 thus directs the mixed media through the primary inlet conduit 26 to the handpiece 31. The vacuum pump 35 may be provided with a gauge 36 to facilitate monitoring and control of the vacuum pressure. A waste canister 37 is coupled to the return conduit and adapted to receive the waste materials drawn from the handpiece 31.

The handpiece 31 is applied to the target area of a patient to perform microdermabrasion while administering the growth factors. Since the microdermabrasion creates an abrasion wound to the target skin area, the addition of oxygen, in addition to the growth factors, facilitates healing and a quicker restoration of the abraded area. The oxygen can thus be mixed in with conventional microdermabrasion media as well as with other media, such as vitamins and other growth factors.

After microdermabrasion is performed with the administration of the growth factors, the used media is drawn through the return conduit 33 by the vacuum pump 35. The used media may be directed to a storage canister 37. The first preferred embodiment of the apparatus 10 shown in FIG. 1 thus comprises a dry system and an associated method wherein the growth factors are applied in a dry form.

In FIG. 2, a preferred embodiment of microdermabrasion system 40 is shown in schematic view. The system 40 may include pressurized input provided by a pressure pump 42. The pressure pump 42 is powered by a power source 44 and may be controlled by a switch 46, such as a foot switch or a switch provided on the handpiece 31. In the system 40, the pressure pump 42 is provided upstream from the supply sources 20, 22 so as to add positive pressure. The combination of the downstream vacuum pump 35 and the upstream pressure pump 42 increases the control and velocity capacity of delivering the cutting material. Air drawn in by the vacuum pump 35 may be recirculated in the system 40 to provide positive pressure. The handpiece 31 may include a plurality of venturi nozzles which produce a jet stream venturi effect.

Furthermore, the positive pressure pump 42 and vacuum source 35 may be used to create a pneumatic undulating effect on the target skin area, which facilitates and circulation and healing of the area. In use, a suction force is applied to the target area and forms a seal between the distal end of the handpiece 31 and the target area. The target area and a space within the handpiece thus form a vacuum chamber With the vacuum source continuously applied, the suction force from the vacuum source 35 draws the target area toward or into the handpiece 31. The suction force also draws blood toward the surface of the skin. Positive pressure from the pump 42 may be simultaneously applied on a target skin, temporarily pushing the area away from the handpiece 31.

The positive pressure is preferably in the form of a jet or stream of pressurized air. The pressurized air is applied in bursts or pulses that impinge on the target area. The pressurized air also enters the space in the handpiece 31 that normally forms the vacuum chamber. Hence, during the bursts or pulses, the pressure in the space rises. The net result is a rise and fall in pressure in the space and vacuum chamber. In fact, when the pressurized air has a large enough flow rate and a high enough pressure, an actual push/pull effect is caused. The resulting undulating effect massages the target skin area and thereby increases the circulation. Massaging in this manner also breaks up fat and promotes the formation of collagen. At the same time, the target area is repeatedly and flexibly brought into contact with the abrasion element. Therefore, while the undulating effect facilitates dermabrasion, it also promotes healing of the skin as well. The jet also massages the target area.

While the undulating effect has been described above as being provided by a specific combination of vacuum and pressurized air applied to the vacuum chamber, it is to be explicitly understood that the undulating effect can be accomplished with any of a variety of combinations of vacuum and pressurized air. For example, the vacuum pressure could be pulsed by itself or in combination with the pressurized air. Thus, the above descriptions are to be taken by way of example and not by way of limitation.

In FIG. 3, a preferred embodiment of a growth factor delivery apparatus 50 is shown in schematic view. In particular, a "wet" delivery apparatus 50 and associated wet method is illustrated in FIG. 3. The apparatus 50 includes an oxygen source 52 that is coupled to a supply 54 of growth factors in water. A valve 56 is provided along an oxygen inlet conduit 58 to control the inclusion of oxygen. A primary inlet conduit 61 is coupled to the liquid growth supply 54 and a handpiece 63.

In operation, oxygen is mixed with the liquid growth supply 54. The oxygenated liquid growth supply is then administered through the handpiece 63. A vacuum pump 65 draws the used liquid through a return conduit 67. A waste canister 69 coupled to the return conduit 67 receives waste materials drawn from the handpiece 63. The apparatus 50 may be provided as a stand-alone apparatus or in a combined system with a microdermabrasion apparatus as discussed further below.

FIG. 4 illustrates a second preferred embodiment of a wet growth factor apparatus wherein the growth factors are housed in a handpiece 63a. In FIGS. 4 and 5, elements of structure similar to those previously discussed are designated by the same reference numeral followed by the letter "a". Thus, the apparatus 50a includes an oxygen source 52a that is coupled to a water supply 54a. A valve 56a is provided along an oxygen inlet conduit 58a to control the inclusion of oxygen. A primary inlet conduit 61a is coupled to the water supply 54 and a handpiece 63a.

In operation, oxygen is mixed with the water. The oxygenated water is then administered through the handpiece 63a. A vacuum pump 65a draws the used liquid through a return conduit 67a. A waste canister 69a coupled to the return conduit 67a receives waste materials drawn from the handpiece 63a. The apparatus 50 may be provided as a stand-alone apparatus or in a combined system with a microdermabrasion apparatus as discussed further below.

FIG. 5 is a close-up, schematic view of the handpiece 63a. In particular, the handpiece 63a includes a growth factor supply 70 that is stored in a vial or cartridge 72. The cartridge 72 is sealed with a membrane 74 that may be punctured by a needle 76, for example. An O-ring 78 may be provided to form a seal with the inserted needle 76. The needle 76 is coupled to a valve 81 that may be adjusted by an external knob 83 to control the rate at which the growth supply 70 is introduced to the water 85 flowing through a primary channel 87, thereby controlling the concentration of growth factors in the water. As an example and not by way of limitation, the growth supply 70 may comprise a liquid that is added to the water via droplets, similar to an intravenous drip line. It should be noted that the external knob 83 may be replaced by a control at any location on the handpiece, or positioned remotely. The handpiece 63a includes a tip portion 90 that facilitates targeted application of the microdermabrasion media and growth factors. In particular, a nozzle 92 directs the materials toward an aperture 94 through which a portion of a patient's skin 96 enters. After application to the skin 93, the used materials are drawn by the vacuum source 65a through a return line 67a.

Since growth factors can be expensive, it will be appreciated that the preferred embodiment illustrated in FIGS. 4 and 5 increases efficiency by enabling a precisely controlled amount of growth factors to be applied to the water. The valve 81 may be configured to shut off and seal the cartridge 72 thus saving the unused supply 70 for future use.

In FIG. 6, a combined system 100 includes a microdermabrasion apparatus 102 and a wet growth factor apparatus 50. The microdermabrasion apparatus 102 includes an abrasion handpiece 104 while the wet growth factor apparatus 50 includes a separate handpiece 63. A common control unit 106 may be employed for the system 100 and coupled to each handpiece 63, 104. The control unit 106 may include a common pump system, which may include a vacuum source and/or a positive pressure source, to alternatively operate each handpiece 63, 104. A switch 108 may be provided on the control unit 106 to alternate the operation of the pump system between the handpieces 63, 104. The microdermabrasion media may be stored in the control unit 106. The growth material may be stored in the control unit 106 or in the fluid delivery handpiece 63 as described above.

FIG. 7 is a schematic view of a preferred embodiment of a growth factor fluid delivery system 120 wherein the growth material is disposed in a handpiece 122. In FIG. 7, a preferred embodiment of a stand-alone delivery system 120 is illustrated. As discussed above, however, it is to be expressly understood that the delivery system 120 may be incorporated into a combined system that also includes a microdermabrasion apparatus. A tube 124 couples the handpiece 122 to a vacuum source 126. A water, or fluid, filter 128 is provided on the tube 124. The handpiece 122 includes a removable, ultrasonic tip 131 that is electrically coupled to a ultrasound unit 133. It is to be expressly understood that the ultrasonic tip 131 may be mounted to any of the handpieces disclosed herein.

FIG. 8 is a close-up, exploded view of the handpiece 122. The handpiece 122 includes a housing 135 that defines a chamber 137 for receiving a cartridge 139. The cartridge 139 stores fluid containing the growth factor(s). The handpiece 122 specifically depicts a vacuum handpiece 122. However, handpiece 122 can be used in any system. For example, the handpiece 122 could be implemented in the system of FIG. 6 in place of handpiece 63. As with the FIG. 6 embodiment, a switch 108 may be provided to enable the user to select vacuum suction handpiece 122, and/or the positive pressure handpiece 104. In the preferred embodiment, the vacuum suction is applied continually while the positive pressure is applied intermittently. An inner portion 142 of the housing 135 is configured to removably secure the cartridge 139 without sealing off the tube 124. For example, the housing inner portion 142 may include axially extending tabs 144 which are radially spaced apart from each other. A fluid passageway 146 is defined between an outer surface 148 of the cartridge 139 and the inner surface 149 of the housing 135, as further shown in FIG. 12. Since the fluid passageway 146 is not sealed from the tube 124, the passageway 146 is in constant fluid communication with the tube 124.

Prior to assembly, the cartridge 139 may be provided with a removable cap 151 which covers an applicator 153 located at a distal end 155 of the cartridge 139. With the cap 151 removed and the cartridge 139 inserted into the chamber 137, a removable handpiece tip 157 is coupled to the housing 135. As an example and not by way of limitation, the tip 157 may include internal threads that register with external threads 159 on the housing 135. A variety of other securing mechanisms, including for example, snap-fit or bayonet type fasteners, may be used that allow for the tip 157 to be removed. The tip 157 defines a central hole 162 through which the applicator 153 is disposed. A plurality of vacuum ports 164 are disposed radially around the central hole 162.

FIGS. 9–11 illustrate different applicators 153-1, 153-2, 153-3, respectively, that may be employed. A variety of other applicators may be employed so long as they can apply the fluid within the cartridge onto a target skin area. For example, in FIG. 9, a roller, or ball, 153-1 applicator is provided. A sponge applicator 153-2 is employed in FIG. 10 while a membrane applicator 153-3 is illustrated in FIG. 11.

For simplicity, elements in the embodiment of FIG. 12, which are analogous to those in the previous embodiment, are designated by the same reference numeral followed by the letter "b". FIG. 12 is an axial, cross-sectional view of the handpiece 122b in operation. The cartridge 139 is configured within the handpiece 122b such that as the handpiece 122b is applied to a target area 166b, the applicator 153b contacts the skin 166b. In operation, the vacuum source creates a suction force in a proximal direction as indicated by arrow 168. This helps draw fluid out of the cartridge 139b, which fluid is applied onto the skin 166b by the applicator 153b. The suction force also draws the isolated piece of skin toward the applicator 153b. The ultrasonic tip 157 facilitates absorption of the growth factors by opening the pores of the skin. The vacuum source removes any excess fluid by drawing the fluid along the fluid passageway 146b into the tube 124.

In FIGS. 13 and 14, the optional ultrasonic tip is omitted in a further preferred embodiment 220. Instead, the housing 222 includes an integral tip 224. In FIG. 14, interior ribs 226 are provided which securely receive the cartridge 139.

A further preferred embodiment of a handpiece 320 is illustrated in FIGS. 15–17. For simplicity, elements in this embodiment which are analogous to those in the previous embodiment are designated by the same reference numeral followed by the letter "c". The applicator is generally referenced by the numeral 153 since it may comprise a variety of different structures as described above, for example, in connection with FIGS. 9–11. The handpiece 320 includes a housing 370 that includes an integral tip 372. The housing 370 defines a lateral slot 374 large enough for inserting and removing a cartridge 139c. Sealing elements 376 provided around the slot 374 form a seal with the inserted cartridge 139c so as prevent leakage of any fluid in the fluid passageway 146c. The distal tip 372 defines vacuum ports 164c. The tip 372 also includes an annular, beveled edge 378. When viewed in profile as shown in FIG. 16, the beveled edge 378 is concave with respect to the skin 366, thereby causing the target area to move closer to the applicator 153 when the handpiece 320 is pressed against the skin 366. In addition to being beveled, the distal-most portion of the tip 372 is rounded to facilitate smooth travel over the surface of the skin while still maintaining a seal.

With respect to FIGS. 7–17, the growth material has been predominantly described as being stored in the handpieces 122, 320. However, the growth material can be stored remotely such as in the control units 106, 126 as they may be used in combination with the embodiments of FIGS. 7–17.

A modular microdermabrasion system 400 according to the invention is illustrated in FIG. 18. For example, an apparatus according to the invention may comprise a microdermabrasion module 410 in combination with a growth factor module 420. As discussed above in connection with FIG. 6, the microdermabrasion 410 and growth factor module 420 may be provided in a single unit (shown as 106 in FIG. 6). In addition to the microdermabrasion module 410 and the growth factor module 420, an apparatus according to the invention may also comprise an enhancer module 430 that enhances the application and/or absorption of the growth factors. As examples and not by way of limitation, the enhancer module 430 may comprise a vacuum 432, ultrasound 434, and/or a pressure spray 436. It is to be expressly understood that the enhancer module 430 may comprise any mechanism or procedure that can massage the skin, provide an undulating effect, open pores, or affect the target skin area in any other manner so as to enhance the reception of the growth factors in order to promote healing. It is to be further understood that any such mechanism included in the enhancer module 430, such as the vacuum 432 or ultrasound 434, may be employed individually or in combination with other mechanisms. For example, an apparatus according to the invention may include a pressure spray 436 to "push" the skin, a vacuum 432 to "pull" the skin, and an ultrasonic device 434 to open the skin's pores.

It will be appreciated that in these embodiments 120, 220, 320, the cartridge may be easily assembled and disassembled. A system and method is thus provided for employing disposable cartridges in fluid delivery handpieces. Once the fluid growth fluid is depleted, an old cartridge may be easily removed and discarded, and replaced with a new loaded cartridge.

In all the preferred embodiments, it will be appreciated that a method and system is provided for effective delivery of growth materials to an abraded area. Whether the growth material is dry and mixed in with the abrasion media or wet and delivered separately, the abraded skin area is immediately treated with the growth material so that the growth factors enter into pores of the skin. Such instantaneous application of the growth factors leads to more efficacious treatment and, thus, facilitates quicker healing than conventional techniques.

The efficiency provided by the methods and apparatuses according to the invention also leads to cost savings as patients can avoid not only a second trip to the treatment facility, but expensive lotions and vitamins as well. Though patients may be encouraged to follow up an abrasion process with vitamins, lotions, and other skin care products, the necessity of such products will be significantly reduced as the instantaneous application of growth factors provides the most effective healing by penetrating the open pores of an abraded area.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A microdermabrasion apparatus, comprising:
   a supply of abrasion media;
   a supply of growth material;
   at least one handpiece to apply the abrasion media and the growth material to a target area;
   a source of oxygen in communication with the handpiece; and
   a mechanism for removing the abrasion media from the target area.

2. The apparatus of claim 1, wherein the growth material is dry.

3. The apparatus of claim 2, wherein the growth material is mixed with the abrasion media.

4. The apparatus of claim 1, further comprising a valve to control a flow of the oxygen to the handpiece.

5. The apparatus of claim 1 wherein the mechanism comprises a vacuum source.

6. The apparatus of claim 5, wherein the vacuum source is disposed downstream from the handpiece, the apparatus further comprising a positive pressure source disposed upstream from the handpiece.

7. A fluid delivery apparatus for applying a fluid to a target skin area, comprising:
   a handpiece comprising a housing;
   a cartridge disposed substantially within the handpiece, the cartridge holding a supply of fluid and including an applicator adapted to apply the fluid to a target skin area; and
   a vacuum source coupled to the handpiece and adapted to draw the fluid out of the cartridge and through the applicator; wherein a space is defined within the housing and exterior to the cartridge; and the space is in communication with the vacuum source.

8. The apparatus of claim 7, wherein the applicator comprises a sponge.

9. The apparatus of claim 7, wherein the applicator comprises a roller.

10. The apparatus of claim 7, wherein the applicator comprises a membrane.

11. The apparatus of claim 7, wherein the housing is adapted to slidingly receive the cartridge.

12. The apparatus of claim 7, wherein the handpiece comprises a beveled distal portion adapted to contact the target skin area.

13. The apparatus of claim 7, wherein the handpiece comprises a distal portion with a plurality of vacuum ports, the vacuum ports disposed axially about the applicator.

14. The apparatus of claim 7, wherein the handpiece comprises a housing with a removable cap to facilitate assembly and removal of the cartridge.

15. The apparatus of claim 7, wherein the supply fluid contains at least one growth factor.

16. The apparatus of claim 7, wherein the housing comprises a distal portion adapted to form a seal with the target skin area.

17. The apparatus of claim 16, wherein the space is sealed off from any area exterior to the handpiece when the housing forms the seal with the target skin area.

18. A method for microdermabrading skin, comprising the steps of:
   abrading a target skin area with microdermabrasion media with a first handpiece;
   applying growth material to the target skin area with a second handpiece;
   retrieving the microdermabrasion media from the target skin area;
   retrieving at least a portion of the growth material from the target skin area; disposing the growth material in an aqueous solution; and further disposing the aqueous solution with the growth material upstream from the second handpiece.

19. The method of claim 18, wherein the growth material is dry, the method further comprising the step of:
   mixing the dry growth material with the microdermabrasion media prior to the applying step.

20. The method of claim 18, further comprising the step of carrying the aqueous solution with the second handpiece.

21. The method of claim 20, wherein the step of disposing the aqueous solution with the growth material within the second handpiece comprises the step of retaining the aqueous solution with a cartridge carried by the handpiece.

22. The method of claim 21, further comprising the step of:

disposing an applicator on a distal end of the cartridge, and wherein the step of applying the growth material to the target skin area with the second handpiece comprises contacting the target skin with the applicator.

23. The method of claim 22 wherein the step of disposing the applicator on the distal end of the cartridge comprises disposing a sponge applicator.

24. The method of claim 22 wherein the step of disposing the applicator on the distal end of the cartridge comprises disposing a roller applicator.

25. The method of claim 22 wherein the step of disposing the applicator on the distal end of the cartridge comprises disposing a membrane applicator.

* * * * *